United States Patent [19]

Bush

[11] Patent Number: 5,755,762
[45] Date of Patent: May 26, 1998

[54] MEDICAL LEAD AND METHOD OF MAKING AND USING

[75] Inventor: M. Elizabeth Bush, Fremont, Calif.

[73] Assignee: Pacesetter, Inc., Sunnyvale, Calif.

[21] Appl. No.: 663,850

[22] Filed: Jun. 14, 1996

[51] Int. Cl.⁶ .............................. A61N 1/05; A61N 5/04
[52] U.S. Cl. .............. 607/122; 607/116; 607/121; 607/123; 607/125; 607/126; 607/127; 607/128; 600/372; 600/388; 600/374
[58] Field of Search .................... 607/116, 121, 607/122, 123, 125, 126, 127, 128; 128/642, 639; 600/372, 373, 374, 388

[56] References Cited

U.S. PATENT DOCUMENTS

| | | | |
|---|---|---|---|
| 4,033,357 | 7/1977 | Helland et al. | 128/418 |
| 4,442,841 | 4/1984 | Uehara et al. | 128/635 |
| 4,557,957 | 12/1985 | Manniso | 428/36 |
| 4,573,480 | 3/1986 | Hirschberg | 128/784 |
| 4,743,480 | 5/1988 | Campbell et al. | 428/36 |
| 4,840,186 | 6/1989 | Lekholm et al. | 128/784 |
| 4,972,846 | 11/1990 | Owens et al. | 128/784 |
| 5,007,435 | 4/1991 | Doan et al. | 128/784 |
| 5,020,544 | 6/1991 | Dahl et al. | 128/714 |
| 5,090,422 | 2/1992 | Dahl et al. | 128/784 |
| 5,231,996 | 8/1993 | Bardy et al. | 128/785 |
| 5,261,419 | 11/1993 | Osypka | 607/122 |
| 5,269,810 | 12/1993 | Hull et al. | 607/129 |
| 5,330,520 | 7/1994 | Maddison et al. | 607/122 |
| 5,358,516 | 10/1994 | Myers et al. | 607/116 |
| 5,466,252 | 11/1995 | Soukup et al. | 607/116 |

OTHER PUBLICATIONS

Draft European Standard "Active Implantable Medical Devices Brady and Tachy Lead Tests Working Draft", Ver. 8.0, Dec., 1995, pp. 1–17.

"Neovascularization of Synthetic Membranes Directed by Membrane Microarchitecture", Brauker, et al., *Journal of Biomedical Materials Research*, Dec. 1995, vol. 29, No. 12, pp. 1517–1524.

Primary Examiner—Jennifer Bahr
Assistant Examiner—Stephen Huang
Attorney, Agent, or Firm—M. Elizabeth Bush; Steven M. Mitchell

[57] ABSTRACT

A continuous sheath of open-celled porous plastic, preferably ePTFE, is used on the outside of an implantable lead, extending along the lead body and the electrodes, in such a way that the lead is isodiametric along its length, and is very strong in tension as is required for lead removal. Because the plastic is open-celled, when the pores are filled with saline, the lead can deliver defibrillation energy through the pores in the plastic. Pore size is chosen to discourage tissue ingrowth while allowing for defibrillation energy delivery through it.

34 Claims, 7 Drawing Sheets

MEDICAL LEAD AND METHOD OF MAKING AND USING

FIELD OF THE INVENTION

The present invention relates generally to medical leads for sensing signals from and delivering electrical energy to body tissues. This invention especially relates to leads for use with implantable defibrillators.

BACKGROUND OF THE INVENTION

A medical lead as referred to herein is an at least partially insulated electrical conductor which interfaces with a patient's body tissue at one end and with a detector and/or energy source at the other. Prior art transvenous defibrillation leads typically have joints where electrodes for sensing and/or energy delivery are connected to their insulated conductors. The joints are typically weaker and larger than the electrode and insulated conductor portions. This makes lead extraction for chronic implants difficult because: 1) the large joints are difficult to pull through the tissue capsule formed around the smaller portions; 2) the weaker joints tend to break, leaving lead fragments in the heart; and 3) the lead body is typically made of silicone or polyurethane insulated coils, and tends to stretch during extraction.

The second and third problems have been addressed in U.S. Pat. No. 5,231,996 to Bardy et al. wherein a lead contains lead body strengthening means, and in U.S. Pat. No. 5,261,419 to Osypka wherein a lead can accept a stylet that engages the distal end of the lead during extraction, in both cases, to minimize elongation and increase tensile strength. However, the problem of varying diameter due to the joints, and resultant difficulty extracting large joints through a small fibrous capsule, remains.

In U.S. Pat. No. 5,090,422 to Dahl et al., which is incorporated herein by reference, a porous coating or sheath is used on an endocardial defibrillation lead to create a dissection plane with respect to adjacent tissue, to substantially prevent tissue ingrowth. However, this does not solve the problem of large, weak joints, as can be seen from the figures in Dahl et al. The coating or sheath does not extend proximal of the electrode, which appears to be much fatter than the lead body. Also, even the portion covered by the coating or sheath does not appear to be substantially isodiametric, as the profile of the helically wound conductor of the electrode can be seen through the coating or sheath. Any substantial increases in diameter in a distal portion as compared with a proximal portion of the lead would make lead extraction more difficult if any adhesions or other tissue ingrowth were not completely eliminated. For the portions of the lead within the vein and cardiac chambers, it is desirable to have no external joints, be isodiametric, be strong in tension with controlled elongation, and have an outer layer that does not promote tissue ingrowth.

In U.S. Pat. No. 5,358,516 to Myers et al., a lead assembly is disclosed having an insulated conductor covered by an ePTFE sheath. This does not, however, solve the problem of large, weak joints, since there is no teaching that the ePTFE sheath continues onto the electrode portions, and a joint would be formed there.

In U.S. Pat. No. 5,330,520 to Madison et al., which is incorporated herein by reference, at least a portion of the outer conductor is surrounded by an outer conductive sheath formed from a suitable material having a non-abrasive effect. To insulate portions of the lead in the non-electrode regions, pores in the conductive porous sheath are filled with a non-conductive polymer. The outer conductive sheath may be a porous polymeric sheath whose pores are infused by a conductive substance such as body fluids or a conductive gel. According to the patent, "one particular advantage of the lead" is that "fibrous ingrowth may occur in the porous portion of the lead, thus securing the lead to the heart wall", implying that a pore size that promotes tissue ingrowth is preferred. However, this would tend to make lead extraction difficult.

It is therefore an object of the present invention to provide a lead that is strong and stretches only minimally in tension.

It is another object of the invention to provide a lead that is essentially isodiametric in critical portions, such as the portion within the vein and cardiac chambers.

It is a further object of the invention to provide a lead that discourages fibrous tissue ingrowth.

SUMMARY OF THE INVENTION

In the present invention, a continuous sheath of open-celled porous plastic, preferably ePTFE, is used on the outside of the defibrillation lead, extending along the lead body and the electrodes, in such a way that the lead is isodiametric along its length, and is very strong in tension as is required for lead removal. Because the plastic is open-celled, when the pores are filled with saline the lead can deliver defibrillation energy through the pores in the plastic. Pore size is chosen to discourage tissue ingrowth. The only portions not covered by the porous plastic are the connector, distal pacing electrode, fixation mechanism, and possibly a bifurcation, trifurcation, or other furcation joint of connectors to the main lead body. The non-electrode portions of the lead are insulated with silicone rubber, polyurethane, non-porous fluoropolymer, or the like, beneath the porous sheath.

As used herein, the term "defibrillation" refers to either or both atrial and ventricular defibrillation.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE PREFERRED EMBODIMENT

Figure 1:
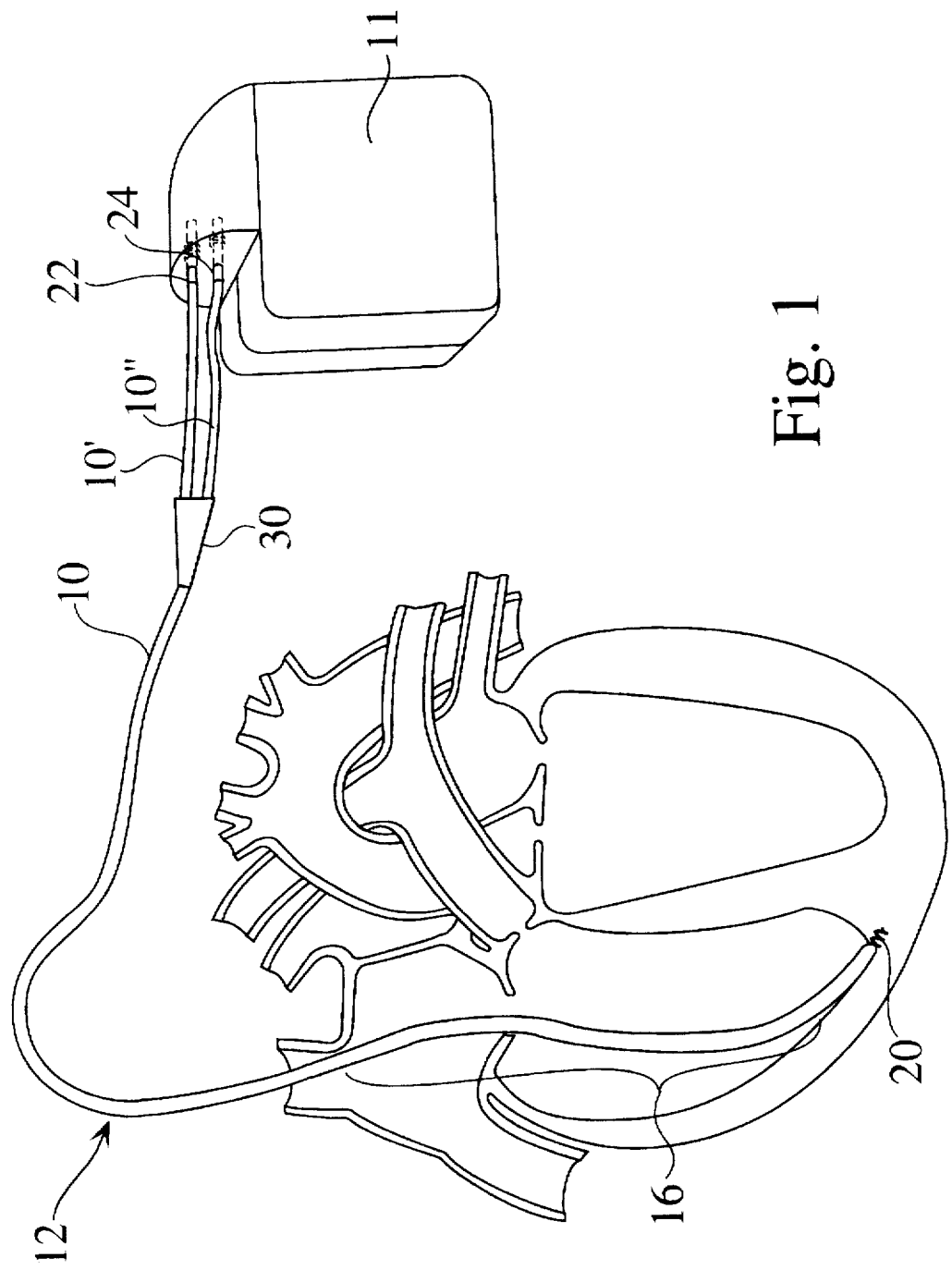
FIG. 1 shows a lead of the present invention having a continuous porous tubular covering on the electrodes and lead body, implanted within the heart.

FIG. 1 shows a lead 12 of the present invention having a continuous porous tubular covering 10 on the electrodes and lead body, implanted within the heart. Additional porous tubular coverings 10', 10" are located on the body of each connector branch 22, 24, which are electrically and mechanically coupled to pulse generator 11. Pulse generator 11 has an electrically active housing for use as an electrode.

Alternatively or additionally, a superior arena cava lead, epicardial lead, or other subcutaneous lead may be used.

Figure 2:
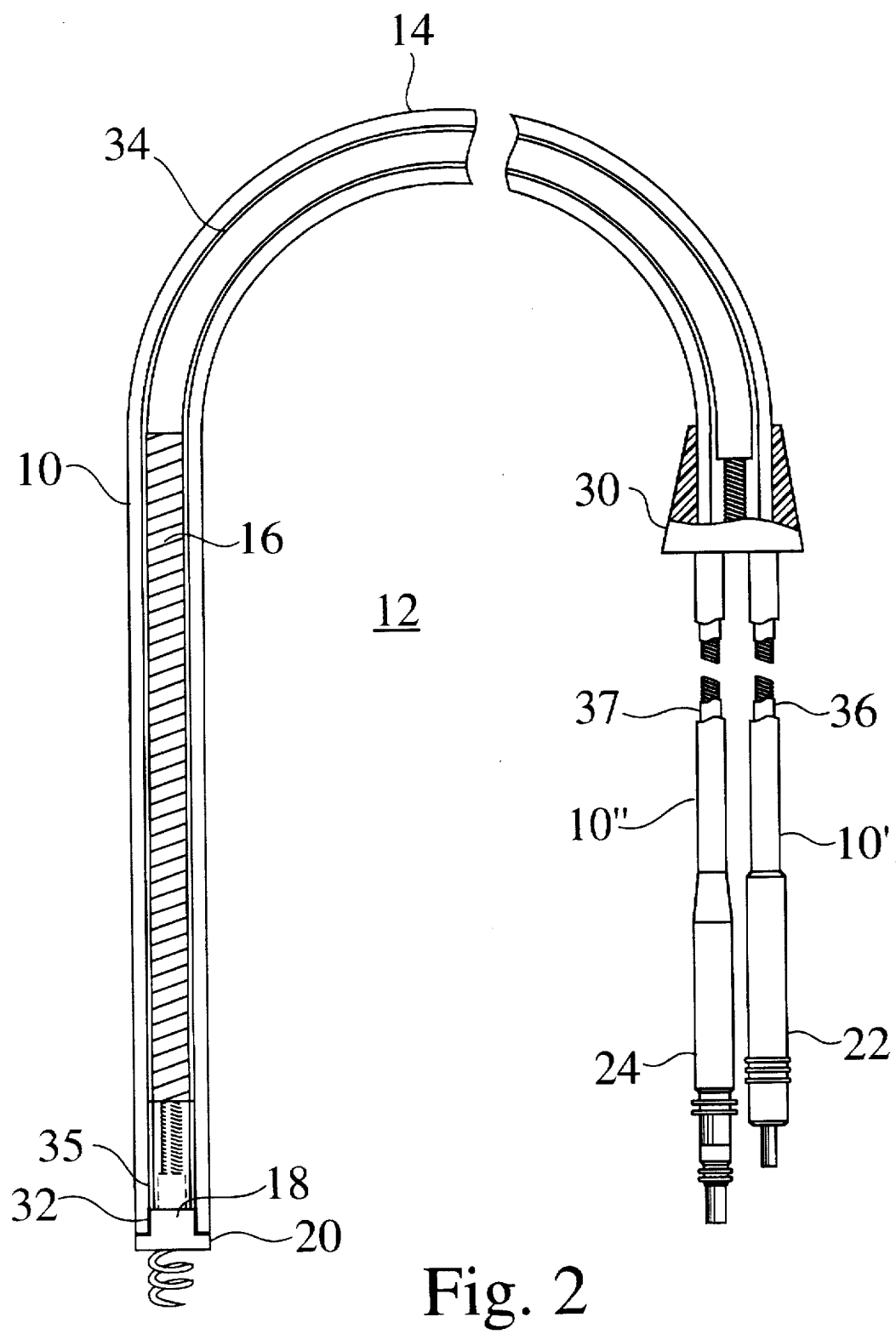
FIG. 2 is a partial cut away view of the lead of FIG. 1.

FIG. 2 is a partial cut away view of lead 12 of FIG. 1. A continuous sheath of open-celled porous plastic, preferably ePTFE, is used as a porous tubular covering 10 on the outside of a defibrillation lead 12. Covering 10 extends along a lead body 14, an electrode 16 and a shank 18 of a distal pacing electrode 20. Lead 12 is isodiametric along its length, and is very strong in tension as is required for lead removal. Because the plastic is open-celled, when the pores are filled with saline or body fluid, lead 12 can deliver defibrillation energy from underlying electrode 16 through the pores in the plastic to the cardiac tissue. Pore size is chosen small enough to discourage tissue ingrowth, but large enough that current can be delivered through covering 10 when its pores are filled with fluid. Underlying electrode 16 may be of any defibrillation or pacing electrode construction known in the art, such as platinum iridium coil, braided carbon fibers, would titanium ribbon, titanium nitride or platinum black coated rings, or coiled platinum iridium coils as described in U.S. Pat. No. 5,439,485 to Mar et al and assigned to the assignee of the present invention.

Alternatively, underlying electrode 16, as well as lead body 14, may be of other constructions that would otherwise be unsuitable were it not for covering 10. For example, electrode 16 and/or lead body 14 may be more mechanically fragile (fragile coatings such as platinum black, lower tensile strength, less fatigue resistant, less abrasion resistant than extruded 50A silicone rubber which is considered to have the lowest accepted abrasion resistance for lead body materials, etc.), less biocompatible (rougher edges, more invaginations, crevices, or places where tissue attachments would otherwise form, etc.), or more complex in overall shape (which would normally be difficult to explant).

Various approved and draft standards exist to provide guidance or list various government agency requirements as to minimum performance requirements of pacemaker and defibrillator leads and other medical devices. These standards and draft standards include prEN 45502# DRAFT EUROPEAN STANDARD, Active Implantable Medical Devices (AIMD) Brady and Tachy Lead Tests Working Draft, Ver. 8.0, December, 1995, which is incorporated herein by reference. Underlying electrode 16 and lead body 14 would not be required to meet the standard on their own, as long as covering 10 provided the means for meeting the standard. For example, in the abovementioned standard, the following language appears:

23. Protection of the active implantable medical device from mechanical forces 23.3 Implantable LEADS shall withstand the tensile forces that might occur after implantation without fracture of any conductors or joints or breaching of any functional electrical insulation.

23.3.1 Test samples

The samples intended for test shall be in the condition as shipped to the customer.

23.3.2 Procedure

The specimen is totally immersed in a bath of approximately 9 g/l saline for a minimum of 10 days at 37° C.±5° C. The specimen is then rinsed in distilled or deionized water and wiped free of surface water.

The LEAD specimen is clamped at the metallic surface of the LEAD connector pin and at the appropriate part of the distal end of the LEAD. The length between these two points shall be measured prior to the application of any tensile load.

The specimen is subjected to a minimum tensile load of 5N or a maximum 20 percent elongation, whichever occurs first, for a minimum duration of one minute. The tensile load is then removed. The tensile load application is repeated for each combination of tip distal end and LEAD connector pin.

23.3.3 Test results

The LEAD shall exhibit no permanent functional damage, or permanent elongation in excess of 5 percent unless the LEAD is intended by the manufacturer to accommodate a longer permanent elongation.

Using the above test procedure to test the underlying electrode 16 and lead body 14 without covering 10 (ignoring 23.3.1) may result in permanent functional damage, or permanent elongation in excess of 5%; this result would be acceptable if, by adding covering 10, the leads pass the test.

As another example, in the same standard, still section 23, the following language defines the AIMD bell mouth test.

23.5 Implantable LEADS shall withstand the flexural stresses that might occur after implantation, without fracture of any conductors.

23.5.1.1 Test samples

The test samples, whether in the form of complete LEADS or LEAD body segments, shall be preconditioned the same way as fully assembled and shipped product.

23.5.1.2 Test procedure

The test is performed in dry conditions and at room temperature.

The LEAD test segment is mounted to hang vertically under gravity in a holding fixture . . . which has an inside dimension that provides a maximum clearance of 10 percent larger than the maximum design width of the test segment. At the lower end of the fixture the inside surface is formed into a bell mouth having a fixture radius such that when the test segment conforms to the contour of the fixture the center line of the test segment at the maximum design width forms a 6 mm±0.1 mm center line bending radius. The fixture is mounted in a machine that pivots the fixture ±90° from the vertical and forces the test segment to flex in the bell mouth of the fixture. A load sufficient to assure that the center line of the test segment conforms to the bending radius is attached to the lower end of a thin, flexible line (cord) strung through the test segment. For LEAD bodies with no accessible lumen, a minimal tensile load may be applied to make it conform to the bending radius.

The test segment is mounted in a fixture having a fixture radius such that the center line of the test segment forms a 6 mm±0.1 mm bending radius, and the conductor is oriented in the worst case test condition when the test segment allows multiple orientations (see the example below for determining the fixture radius). The fixture is then oscillated 90°+, −5° each side of vertical at a rate of approximately 2 Hz for a minimum of 47 000 cycles.

The test is repeated for each unique uniform flexible part of the LEAD body.

23.5.1.3 Test results

Compliance is confirmed if the measured DC resistance of each conduction path is within the manufacturer's specifications adjusted for the length of the LEAD segment under test, and each conductor is functionally intact per the manufacturer's performance specification.

Using the above flex test procedure to test the underlying electrode 16 and lead body 14 without covering 10 may result in a conductor that is not functionally intact; again, this result would be acceptable if, by adding covering 10, the leads pass the test.

In conventional leads, the length of the right ventricular (RV) defibrillation electrode 16 is limited by the length of the RV chamber because of danger of trauma to the tricuspid valve. Because of the nonfibrosing nature of lead 12, and its isodiametricity, the defibrillation electrode can be made longer than in conventional leads because trauma to the tricuspid valve and potential ingrowth into it is drastically reduced.

The only portions of lead 12 not covered by porous tubular covering 10 are lead connectors 22, 24, distal pacing electrode 20, and a joint 30 of connectors 22, 24 to lead body 14. Critical portions of lead 12 that are covered are the regions located within the vein and cardiac chambers, with enough extending from the venous entry site to grasp for lead removal. Ideally, covering 10 extends proximally all the way to the connector or the furcation 30 of connectors if there is more than one connector as in FIGS. 1 and 2.

Distally, covering 10 extends over the shank 18 of the distal pacing electrode 20 and attaches to it, using an adhesive 32. In addition to bonding covering 10 to shank 18, adhesive 32 also electrically insulates shank 18 from the cardiac tissue, which is important for decreasing surface area to increase current density for pacing. To improve the mechanical interconnection of the components of the lead, the method of Doan et al. may be used, as described in U.S. Pat. No. 5,007,435, which is incorporated herein by reference. Porous tubular covering 10 may be treated with Chemgrip or by glow discharge (plasma) treatment to activate its surface to enhance adhesion to shank 18 and to silicone medical adhesive 32. A polyurethane glue, comprised of Pellethane® (236375D in N,N-dimethyl acetamide, may be applied to shank 18 and subsequently air dried to enhance adhesion to silicone medical adhesive 32. Adhesion promoters, such as Dow Corning® Z-6020 silane (amino alkyl functional silane), may be applied to metal or plastic components prior to the application of medical adhesive 32 to further improve the mechanical interconnection of the lead components. Alternatively, porous tubular covering may be mechanically attached to shank 18 using a ligature, as discussed in more detail below in connection with FIG. 5.

The conductors in lead 12 which electrically and mechanically couple electrodes 16 and 18 to connectors 22 and 24 may be of any structure or combination of structures known in the art, such as coaxial coils separated by an insulating tube, side-by-side cables or coils insulated with a fluoropolymer, silicone, polyimide, or polyurethane, coiled drawn filled tube (DFT, Fort Wayne Metals, Ft. Wayne, Ind.) cables according to U.S. Pat. No. 5,483,022 to Mar, which is assigned to the assignee of the present invention and incorporated herein by reference, or a multiple helix of Leklholm et al. described in U.S. Pat. No. 4,840,186 and incorporated herein by reference. Preferably, the nonelectrode portions of lead 12 are electrically insulated with an insulator 34, 35, 36, 37 which may be silicone rubber, polyurethane, or nonporous fluoropolymer tubing located between coaxial coiled conductors and beneath porous tubular covering 10, as described in U.S. Pat. No. 5,358,516 to Myers et al. Alternatively, multiple conductors may lie side by side, and may be individually insulated with a fluoropolymer coating, silicone tubing, or the like. As another alternative, the pores of porous tubular covering 10 may be filled with an insulating material in the nonelectrode portions of the lead; however, care must be taken in material choice to ensure that the structure is not altered from a nonfibrosing structure to one that produces fibrous tissue ingrowth.

Porous tubular covering 10 may be made of a fluoropolymer, polyester, polyurethane, cellulose acetate, mixed esters of cellulose, acrylic copolymer on nylon support, polyvinyl difluoride, polysulfone, polypropylene, cellulose nitrate, polycarbonate, nylon, and polyethylene. Preferably, the covering material is a fluoropolymer such as PTFE, FEP, or PFA, and most preferably, PTFE. Covering 10 may be a composite of two or more materials, such as a laminate of acrylic copolymer on a nylon support. The structure of tubular covering 10 is preferably expanded, such as expanded polytetrafluoroethylene, but may alternatively be woven, felt, fused mesh, or the like.

The structure of the outer surface of porous tubular covering 10 is preferably chosen to reduce fibrous ingrowth. However, the inner layers of tubular covering 10 may have larger pores, which would allow more saline within the material, thereby increasing conductivity, as would be desirable in regions covering electrode 16. Overall, the material is characterized by pore sizes suitable to allow penetration of bodily fluids but small enough such that a dissection plane or interface surface is formed so that tissue ingrowth is properly controlled upon chronic placement in the body.

Lead 12 may be supplied in a sealed package with the pores of the tubular covering already filled with saline (vet out). Alternatively, the lead may be supplied with a wet-out agent such as a surfactant, hydrogel or gelatin applied so that the lead automatically wets out almost immediately upon contact with body fluids. Two possible surfactants include dioctyl sulfosuccinate (DSS) and tridodecylmethylammonium chloride (TDMAC). As another alternative, a wet-out agent may be supplied for application just prior to implant. In both cases described that use a wet-out agent, the lead may be soaked in sterile saline prior to insertion into the patient. As yet a further alternative, the lead may be supplied with no wet-out agent, with the pores essentially filled with air; in that case, any electrical testing must occur after sufficient time has been given to wet out the lead, on the order of a few days for expanded polytetrafluoroethylene (ePTFE).

Figure 3:
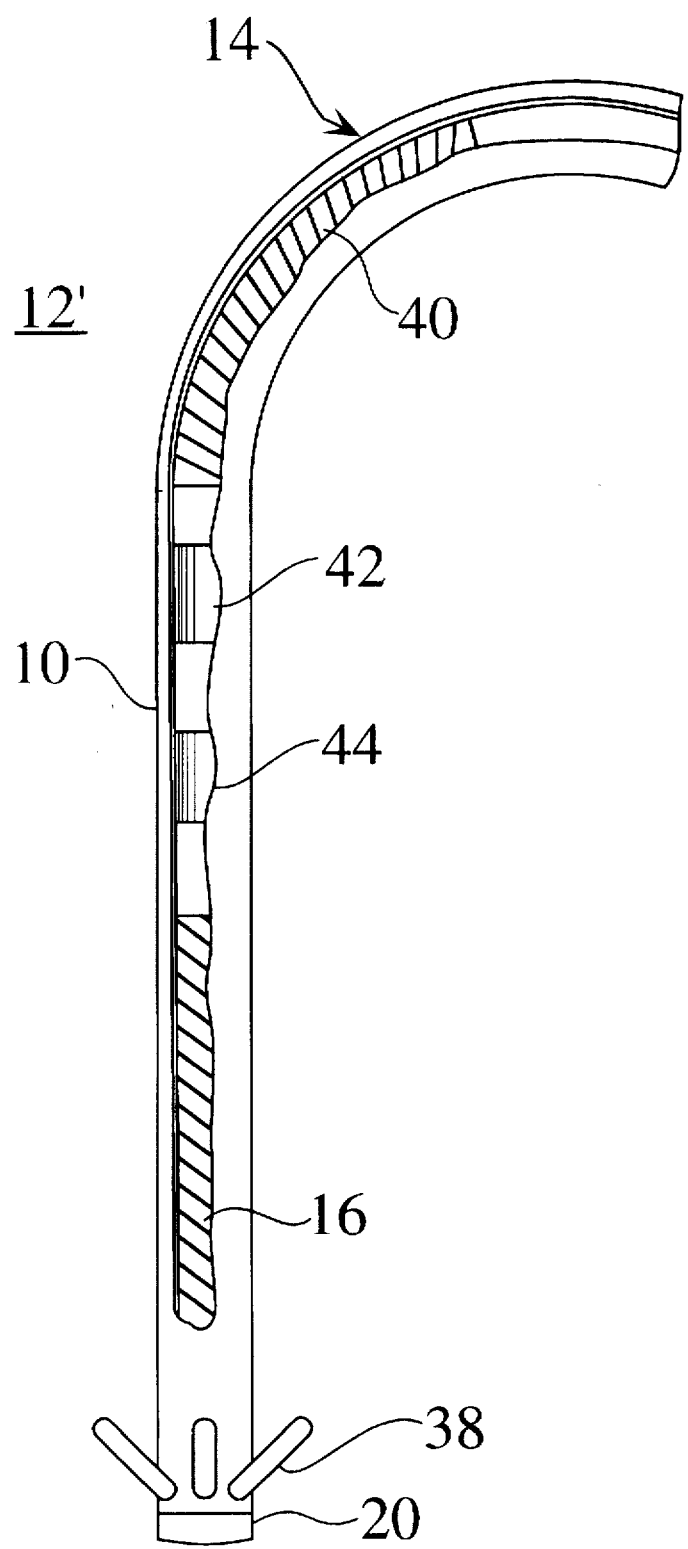
FIG. 3 is a partial cut away view of an alternative embodiment of the lead of the present invention.

FIG. 3 is a partial cut away view of an alternative embodiment of the lead of the present invention. Lead 12' has a tines 38, for anchoring the distal end of the lead into the trabeculae of the patient's heart. In addition to distal pacing electrode 20 and RV defibrillation electrode 16, lead 12' has SVC electrode 40, and two atrial pacing/sensing electrodes 42 and 44. Porous tubular covering 10 extends over lead body 14, electrodes 40, 42, 44, and 16, down to the shank of distal pacing electrode 20. Except for tines 38, the lead is isodiametric from lead body 14 all the way to the distal end of the lead.

Figure 4:
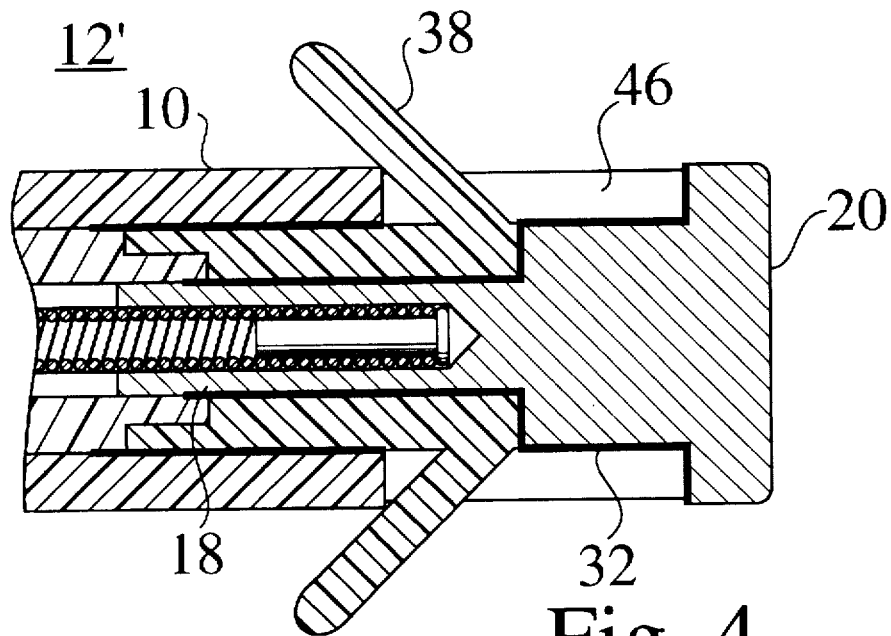
FIG. 4 is an enlarged view of the distal electrode and tine section of FIG. 3.

FIG. 4 is an enlarged view of the distal portion of lead 12' showing distal pacing electrode 20 and tines 38 of FIG. 3. In order to maintain isodiametricity, or at least to keep the most distal portion of the lead body at least as small as the more proximal portions, porous tubular covering 10 is placed over a molded tine section with the individual tines 38 poking through holes or slots 46 formed in tubular covering 10 (slots are shown). Holes or slots 46 may be laser drilled, pierced, punched, or otherwise cut. Adhesive 32 is, used to bond the body of tines 38 to shank 18, and to bond porous tubular covering 10 to the body of tines 38 and to shank 18.

Figure 5:
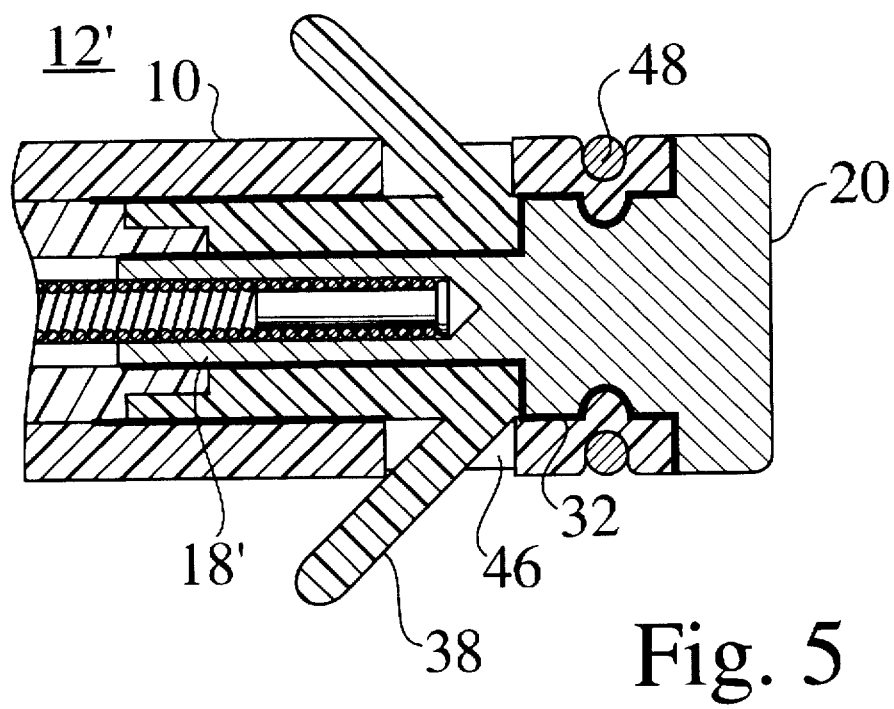
FIG. 5 is an enlarged view of an alternative embodiment of the distal electrode and tine section of FIG. 3.

FIG. 5 is an enlarged view of an alternative embodiment of the distal portion of lead 12' showing distal pacing electrode 20 and tines 38 of FIG. 3. Porous tubular covering 10 is mechanically attached to electrode shank 18 by a ligature, o ring, clamp, or the like 48 placed around covering 10. Preferably, ligature 48 lies in a groove formed within shank 18. In this figure, tines 38 protrude through holes 46 in tubular covering 10.

Figure 6:
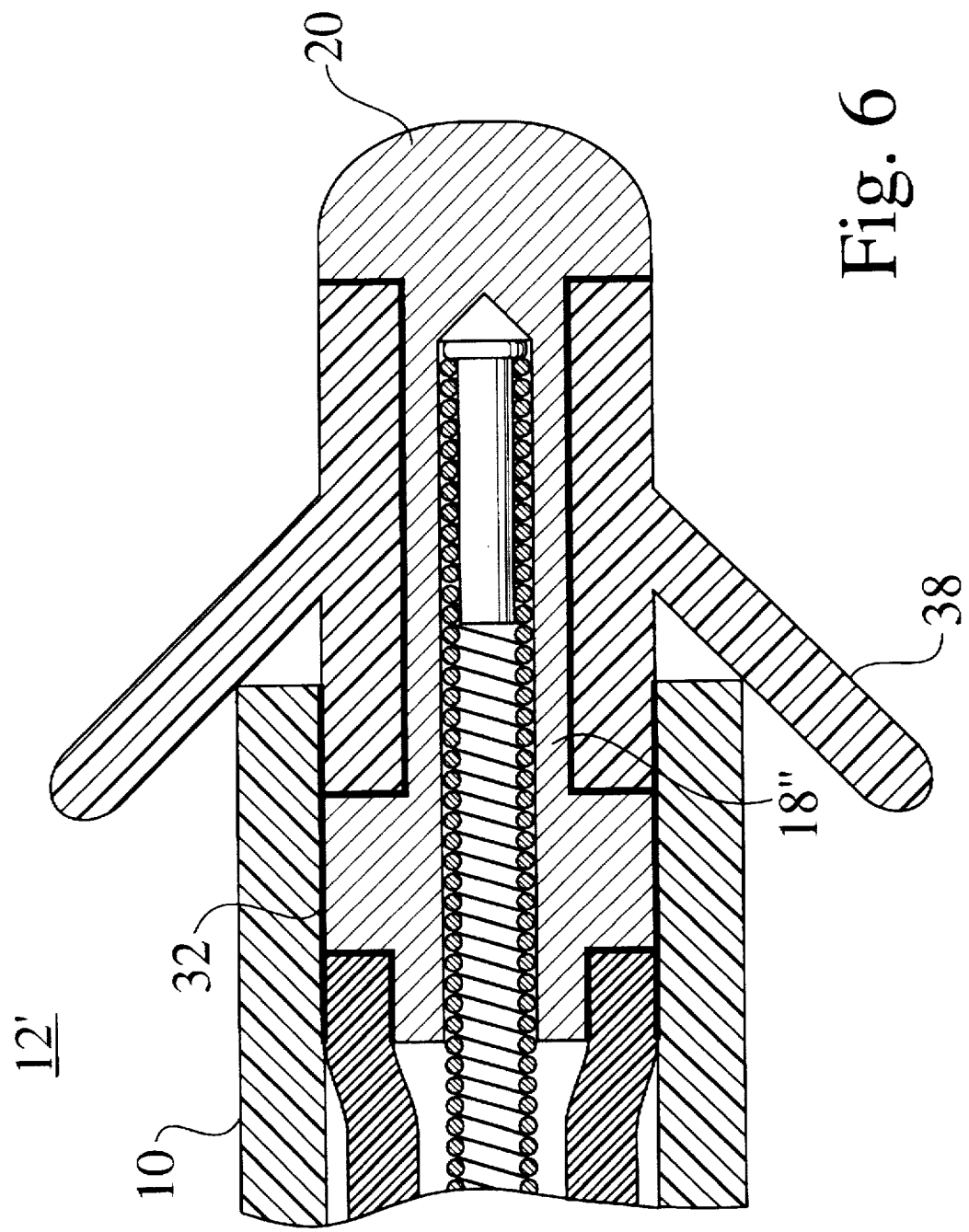
FIG. 6 is an enlarged view of another embodiment of the distal electrode and tine section of FIG. 3.

FIG. 6 is an enlarged view of another embodiment of the distal portion of lead 12' showing distal pacing electrode 20 and tines 35 of FIG. 3. Porous tubular covering 10 is attached to electrode shank 18" and electrically insulated from it by adhesive 32. Tines 35 may be bonded to electrode shank 18" using adhesive 32 as shown, or may be bonded using a different adhesive, or may be molded directly to electrode shank 18". In FIGS. 4–6, porous tubular covering 10 is solidly attached to the distal end of the lead in such a way as to ensure that the lead can be extracted intact, should explant become necessary.

Figure 7:
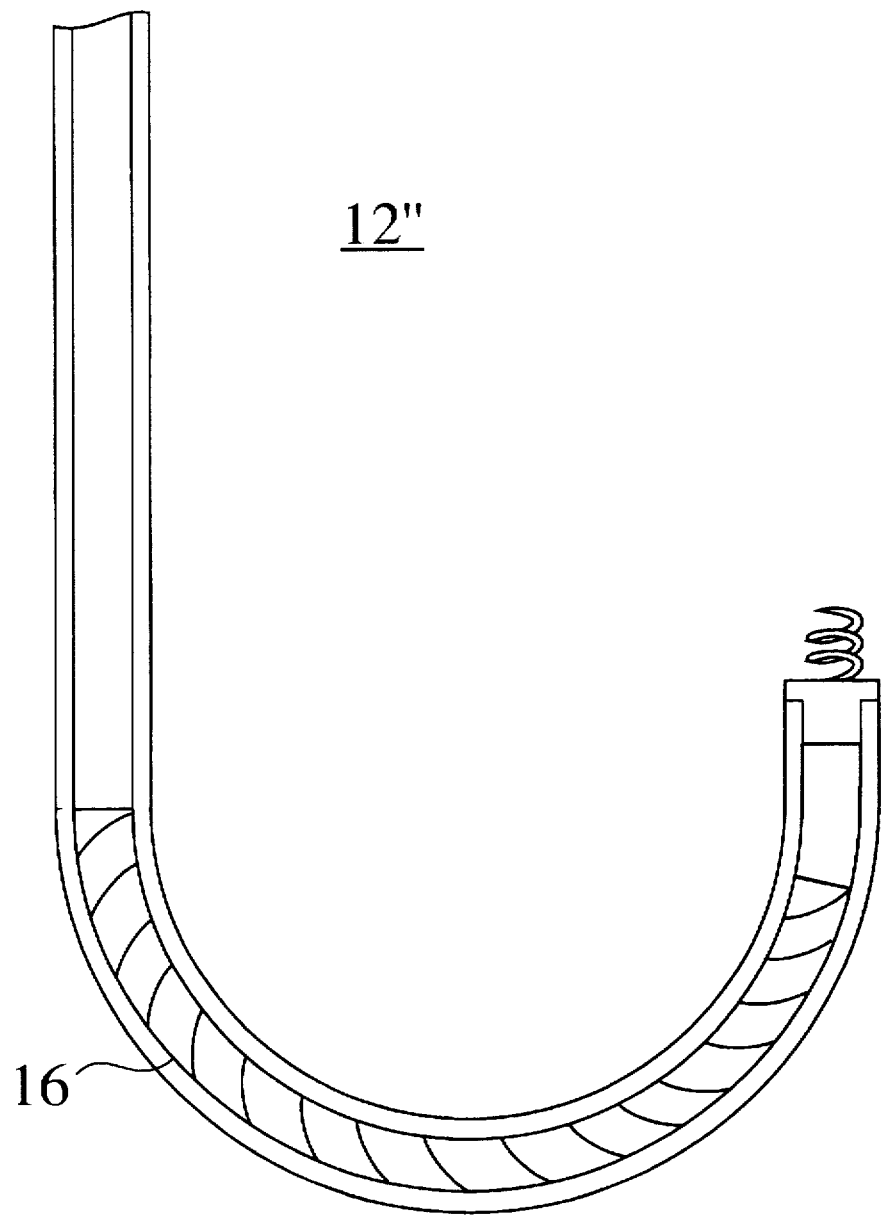
FIG. 7 shows a J lead of the present invention.

FIG. 7 shows a J lead 12" of the present invention which increases the surface area of the defibrillation electrode 16 within the right ventricle. Such "J" configuration can be imparted to the lead in a manner well known in the art.

Figure 8:
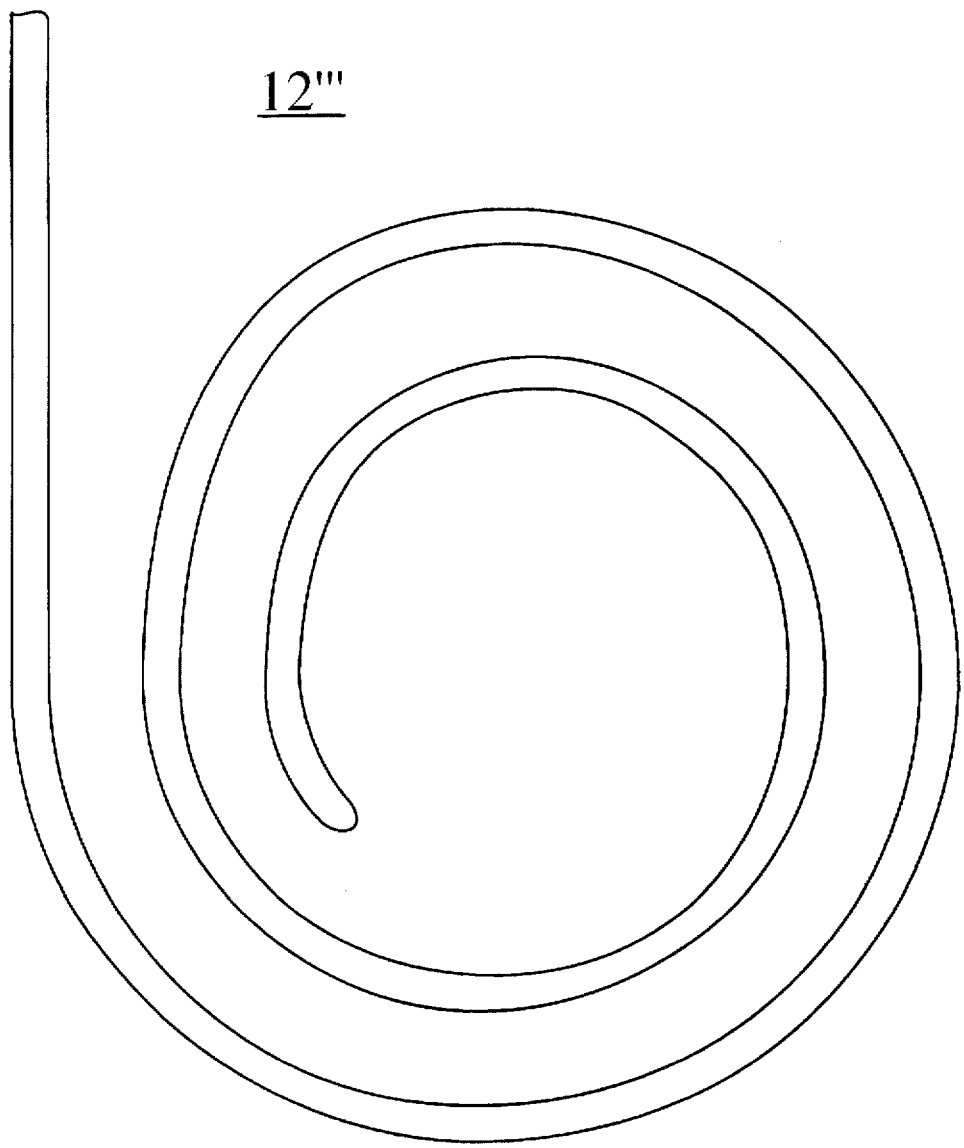
FIG. 8 shows a spiral lead of the present invention.

FIG. 8 shows a spiral lead 12'" of the present invention which may be used endocardially, epicardially, or subcutaneously.

The invention has been described with reference to a preferred embodiment of an implantable endocardial ventricular defibrillation lead. However, the invention could be used for other body implantable leads, such as for subcutaneous or epicardial defibrillation leads, atrial defibrillation leads, and leads for use with pacemakers, neurostimulators, muscle stimulators, and cochlear implants.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable medical lead comprising:
   a lead subassembly comprising an electrode, a conductor electrically coupled to said electrode, and a connector electrically coupled to a proximal end of said conductor; and
   a porous tubular covering extending over at least a portion of said electrode and at least a portion of said conductor, wherein said porous tubular covering has an outer surface pore size such that said porous tubular covering substantially isolates said portion of said electrode and said portion of said conductor from ingrowth of tissue.

2. The lead of claim 1, wherein said tubular covering is substantially isodiametric.

3. The lead of claim 1, wherein said tubular covering is chosen from the group consisting of:
   fluoropolymer, polyester, polyurethane, cellulose acetate, mixed esters of cellulose, acrylic copolymer on nylon support, polyvinyl difluoride, polysulfone, polypropylene, cellulose nitrate, polycarbonate, nylon, and polyethylene.

4. The lead of claim 3, wherein said tubular covering comprises a fluoropolymer chosen from the group consisting of:
   FEP, PTFE, and PFA.

5. The lead of claim 1, wherein said tubular covering comprises a composite or laminate of at least two materials.

6. The lead of claim 1, wherein said porous tubular covering has a structure chosen from the group consisting of:
   expanded, woven, felt, and fused mesh.

7. The lead of claim 1, wherein said tubular covering has an inner surface pore size larger than said outer surface pore size.

8. The lead of claim 1, wherein said porous tubular covering has pores that are at least partially filled by a wet-out agent.

9. The lead of claim 1, wherein said lead is packaged in a sealed package, wherein said package contains saline.

10. The lead of claim 1, wherein said electrode is a defibrillation electrode.

11. The lead of claim 10, wherein said defibrillation electrode has a length greater than 7.5 centimeters.

12. The lead of claim 1, wherein said electrode is a sensing electrode.

13. The lead of claim 1, wherein said electrode is a defibrillation electrode and said lead further comprises a second electrode and a second conductor at least partially covered by said porous tubular covering.

14. The lead of claim 13, wherein said second electrode is a sensing electrode.

15. The lead of claim 1, wherein said porous tubular covering has an inner diameter greater than an outer diameter of said electrode thereby forming a gap between said porous tubular covering and said electrode.

16. The lead of claim 1, and further comprising an electrically insulating layer between said conductor and said porous tubular covering.

17. The lead of claim 16, wherein said porous tubular covering has an inner diameter greater than an outer dimension of said electrically insulating layer thereby creating a gap between said porous tubular covering and said electrically insulating layer.

18. The lead of claim 1, said lead body further including a second conductor coupled between a second connector at said lead body proximal end and a second electrode on said lead body.

19. The lead of claim 1 wherein said lead subassembly is of a construction that, without said porous tubular covering, a 10 day, 37° C., 9 g/l saline soak and subsequent one minute, 5N tensile load application results in permanent elongation greater than 5%.

20. The lead of claim 1 wherein at least a portion of said electrode has a fragile high-surface area coating.

21. The lead of claim 1 wherein said lead subassembly has a low abrasion resistance.

22. The lead of claim 1 wherein said lead subassembly is nonbiocompatible.

23. The lead of claim 22 wherein at least a portion of said lead subassembly has rough edges that would irritate body tissue if implanted without said porous tubular covering.

24. The lead of claim 22 wherein said electrode has crevices that would encourage tissue ingrowth if implanted without said porous tubular covering.

25. An implantable medical lead comprising:
   a lead body having a proximal end and a distal end and including at least one conductor;
   an electrode positioned on said lead body and electrically coupled to said conductor;
   a connector positioned at said proximal end of said lead body and electrically coupled to said conductor; and
   a porous tubular covering having proximal and distal ends and extending over at least a portion of said electrode and at least a portion of said lead body.

26. The lead of claim 25 wherein said distal end of said tubular covering is mechanically coupled to said lead body near said distal end of said lead body, and said proximal end of said tubular covering, is mechanically coupled to said lead body near said proximal end of said lead body whereby said tubular covering completely covers said electrode.

27. A method of making an implantable medical lead comprising the steps of:
   (a) electrically connecting a conductor to a connector;
   (b) electrically connecting said conductor to an electrode; and
   (c) inserting said electrode and conductor into a porous tube having proximal and distal ends.

28. The method of claim 27 and further comprising the step of:
   (d) mechanically attaching said porous tube proximal end to said connector.

29. The method of claim 27 and further comprising the step of:
   (e) mechanically attaching said porous tube distal end near a distal end of said lead.

30. The method of claim 29 wherein said step (e) comprises applying an adhesive to said porous tube and to a distal pacing electrode shank.

31. The method of claim 29 wherein said step (e) comprises tying a ligature around said porous tube and a distal pacing electrode shank.

32. The method of claim 27 and further comprising the steps of:
   (f) forming holes or slots in said distal end of said porous tube; and
   (g) inserting tines positioned on said lead distal end through said holes or slots.

33. A method for implanting a lead having a porous tubular covering extending over at least a portion of an electrode and at least a portion of a lead body comprising the steps of:
   (a) applying a wet-out agent to said lead; and
   (b) positioning said lead within a patient.

34. The method of claim 33, and further including after said step (a) and before step (b), the step of:
   (c) soaking said lead with said wet-out agent in saline.

* * * * *